United States Patent
Widmann

(10) Patent No.: US 11,963,940 B2
(45) Date of Patent: Apr. 23, 2024

(54) PARENTERAL ESMOLOL FORMULATION

(71) Applicant: AOP ORPHAN PHARMACEUTICALS AG, Vienna (AT)

(72) Inventor: Rudolf Widmann, Purkersdorf (AT)

(73) Assignee: AOP Orphan Pharmaceuticals AG, Vienna (AT)

( * ) Notice: Subject to any disclaimer, the term of this patent is extended or adjusted under 35 U.S.C. 154(b) by 0 days.

(21) Appl. No.: 17/582,945

(22) Filed: Jan. 24, 2022

(65) Prior Publication Data

US 2022/0249424 A1  Aug. 11, 2022

Related U.S. Application Data

(63) Continuation of application No. 15/663,645, filed on Jul. 28, 2017, now abandoned, which is a continuation of application No. 14/398,312, filed as application No. PCT/EP2013/059594 on May 8, 2013, now abandoned.

(30) Foreign Application Priority Data

May 10, 2012 (EP) .................................. 12167443

(51) Int. Cl.
| | | |
|---|---|---|
| *A61K 31/24* | (2006.01) | |
| *A61K 9/00* | (2006.01) | |
| *A61K 9/08* | (2006.01) | |
| *A61K 9/19* | (2006.01) | |
| *A61P 9/06* | (2006.01) | |

(52) U.S. Cl.
CPC ............ *A61K 31/24* (2013.01); *A61K 9/0019* (2013.01); *A61K 9/08* (2013.01); *A61K 9/19* (2013.01)

(58) Field of Classification Search
CPC ......... A61K 9/19; A61K 9/0019; A61K 31/24
See application file for complete search history.

(56) References Cited

U.S. PATENT DOCUMENTS

2008/0293814 A1* 11/2008 Tiwari ................. A61K 31/216
514/567

OTHER PUBLICATIONS

"Esmocard LYO 2500 mg powder for concentrate for solution for infusion", CGB-MEB (College ter Beoordeling van Geneesmiddelen-Medicines Evaluation Board), Sep. 7, 2010 (Sep. 7, 2010) (Year: 2010).*
Wiest et al (The Journal of Thoracic and Cardiovascular Surgery, 1998; 115(4):890-897) (Year: 1998).*
Kobayashi et al (Circ J, 2012; 76: 1646-1653) (Year: 2012).*
Federal Register, 2010, vol. 75, No. 86, "Determination that BREVIBLOC (Esmolol HCL) injection, 250-mg/ml, 10-mg/ml amplue, was withdrawn from sale for reasons of safety or effectiveness", 2 pages, May 5, 2010.
Stranz M, A Review of pH and Osmolarity, Int J of Pharm. Comp., 2002, vol. 6, No. 3, pp. 216-220.
Office Action dated Sep. 28, 2023 for corresponding Thai Patent Application No. 1401006745, 9 pages.

* cited by examiner

*Primary Examiner* — Rayna Rodriguez
(74) *Attorney, Agent, or Firm* — LOZA & LOZA, LLP; Michael F. Fedrick

(57) ABSTRACT

A parenteral formulation of esmolol hydrochloride for use in the treatment of a patient suffering from tachycardia comprising a lyophilized powder consisting of pure esmolol hydrochloride, wherein said powder is reconstituted to obtain a ready-to-use i.v. solution of esmolol hydrochloride at a concentration of 20-100 mg/mL, and said i.v. solution is directly administered to the patient, and further a method of producing a ready-to-use i.v. solution of esmolol hydrochloride by reconstituting a lyophilized powder consisting of pure esmolol hydrochloride with a solvent, characterized in that said solvent is an i.v. solvent devoid of alcohol or a buffer excipient, in an amount necessary to obtain a ready-to-use i.v. solution at a concentration of 20-100 mg/mL, and the ready-to-use i.v. solution containing a parenteral formulation of 20-100 mg/mL pure esmolol hydrochloride in an infusion device or consisting of a parenteral formulation of 20-100 mg/mL pure esmolol hydrochloride, WFI and/or saline solution, devoid of any alcohol or buffer excipients.

10 Claims, No Drawings

PARENTERAL ESMOLOL FORMULATION

CROSS-REFERENCE TO RELATED APPLICATIONS

This application is a continuation of U.S. patent application Ser. No. 15/663,645, filed on Jul. 28, 2017 and entitled PARENTERAL ESMOLOL FORMULATION, which is a continuation of U.S. patent application Ser. No. 14/398,312, filed on Oct. 31, 2014, which is the U.S. national stage of International Patent Application No. PCT/EP2013/059594, filed on May 8, 2013, which claims the benefit of priority under 35 U.S.C. § 119 from European Patent Application No. 12167443.6, filed on May 10, 2012. The disclosures of the foregoing applications are incorporated herein by reference in their entirety.

FIELD OF THE INVENTION

The invention refers to a parenteral formulation of esmolol hydrochloride for use in the treatment of a patient suffering from tachycardia and a highly concentrated ready-to-use i.v. solution of esmolol hydrochloride.

BACKGROUND

Esmolol is a parenterally administered, cardioselective beta-inhibitor. The active substance is esmolol hydrochloride (Esmolol HCl, 4-[2-Hydroxy-3-[(1-methylethyl)amino] propoxy] benzenepropanoic acid methyl ester hydrochloride, CAS Number: 81161-17-3), with established efficacy and tolerability. Esmolol is indicated for the short-term treatment of supraventricular tachycardia (except for pre-excitation syndromes), and for the rapid control of ventricular rate in patients with atrial fibrillation or atrial flutter in perioperative, postoperative, or other circumstances where short-term control of the ventricular rate with a short acting agent is desirable. It is also indicated for tachycardia and hypertension during the perioperative phase and noncompensatory sinus tachycardia where, in the physician's judgement the rapid heart rate requires specific intervention. Esmolol is not intended for use in chronic settings.

Brevibloc® 100 mg/10 ml (Baxter Deutschland GmbH) has been provided in a liquid formulation comprising saline, sodium acetate, acetic acid and water for injection (WFI). The product is currently provided as a concentrate 2500 ml/10 mL that is, however, not suitable for direct intravenous (i.v.) injection and must be diluted prior to administration or as a diluted solution using NaCl as a diluting agent (2500 mg/250 mL).

According to the product information of Brevibloc® there is the risk of chronic toxicity; preclinical studies have shown vessel injury and thrombophlebitis at concentrations of 20 mg/mL, thus, it was recommended against using concentrations higher than 10 mg/mL. Upon perivenous administration of at least 10 mg/mL, there are local reactions at the injection site.

The Brevibloc® formulation is prepared according to WO 02/076446 A1, disclosing a formulation comprising the active substance, a buffering agent, like acetate, and an osmotic-adjusting agent, like saline. This formulation is designed as a thermostable solution, which can be sterilized by autoclaving.

WO 2008/153582 A1 discloses a concentrate esmolol formulation, which comprises the active substance at a concentration of 50 mg/mL and a buffering agent, like sodium acetate and acetic acid. Such concentrate is usually diluted before infusion, so to minimize adverse reactions, like local skin irritation at the site of infusion.

"ESMOCARO LYO 2500 mg powder for concentrate for solution for infusion", 7 Sep. 2010, pages 1-13 (URL: http://db.cbg meb.nl/mri/spc/nih-0779-003.pdf) and "PACKAGE LEAFLET: INFORMATION FOR THE USER: ESMOCARO LYO", 9 Nov. 2010, pages 1-8 (URL: http://db.cbg meb.nl/mri/pil/nih-0779-003.pdf) describe an esmolol Lyo wherein the final formulation has a concentration of 10 mg/mL.

While it would be desirable to administer high concentrations of esmolol hydrochloride to shorten the treatment time, there is the risk of infusion site reactions including inflammation and induration, like edema, erythema, skin discoloration, burning at the infusion site, thrombophlebitis, and local skin necrosis from extravasation phlebitis, which side effects are commonly minimized by administering the diluted formulation.

Typically a 2500 mg/10 mL concentrate for solution for infusion is provided for further dilution to obtain a 100 mg/10 mL solution for injection.

WO 2009/079679 A2 describes a storage-stable Esmolol HCl solution comprising cyclodextrin as pharmaceutical solubilizer to ease the dilution of a concentrate.

ESMOCARD LYO (Orpha-Devel Handels and Vertriebs GmbH, Austria) comprises esmolol hydrochloride in the lyophilized form. It is provided as a 2500 mg powder for concentrate for solution for infusion. The reconstituted concentrate contains 50 mg/mL, is further diluted to a concentration of 10 mg/mL.

It is the object of the invention to provide a concentrated i.v. solution of esmolol hydrochloride that can be safely used for the treatment of tachycardic patients.

SUMMARY OF THE INVENTION

The object is solved by the subject matter as claimed.

According to the invention there is provided a parenteral formulation of esmolol hydrochloride for use in the treatment of a patient suffering from tachycardia comprising a lyophilized powder consisting of pure esmolol hydrochloride, wherein said powder is reconstituted to obtain a ready-to-use i.v. solution of esmolol hydrochloride at a concentration of 20-100 mg/mL, and said i.v. solution is directly administered to the patient.

Specifically said powder is reconstituted in an i.v. solvent devoid of alcohol or a buffer excipient. For example, said powder is reconstituted in an aqueous i.v. solvent selected from the group consisting of water for injection (WFI), glucose solution, glucose and Ringer solution, glucose and saline solution, saline solution, Ringer Lactate solution or Ringer Lactate and saline solution.

According to a specific embodiment said powder is reconstituted to obtain an iso-osmotic i.v. solution.

Preferably, said i.v. solution has a pH of 4.5 to 5.0.

Specifically, said powder, comprising e.g. at least 100, at least 250, or at least 2500 mg esmolol hydrochloride, is easily reconstituted with at least 5 mL, or at least 10 mL, alternatively at least 50 mL, in some cases at least 100 mL, at least 250 mL or at least 500 mL, with the i.v. solvent. The reconstitution time at room temperature usually is short, which is a great advantage for the clinician. Depending on the concentration, the i.v. solvent and means for reconstitution, the reconstitution time typically is within 15 seconds up to 5 minutes. As an example, the lyophilized powder containing 2500 mg esmolol hydrochloride is reconstituted in 50 mL WFI within less than 1 min, typically less than 30 sec, in most cases immediately, i.e. within 15 seconds by slight agitation at room temperature.

It is preferred that said esmolol hydrochloride concentration is at least 50 mg/mL.

Said i.v. solution is specifically administered as infusion or continuous infusion.

In particular, said i.v. solution is administered as maintenance infusion, e.g. at a dose of at least 25 µg/kg/min, optionally following an initial infusion, e.g. at a dose of at least 300 µg/kg/min. A start with the maintenance infusion is also possible.

Said initial infusion may specifically be at a dose of at least 300 µg/kg/min, preferably more than 300 µg/kg/min, such as at least 400 or at least 500 µg/kg/min.

Said maintenance infusion may specifically be at a dose of at least 25 µg/kg/min, preferably at least 50 µg/kg/min, or at least 100 µg/kg/min, such as at least 200, at least 300, typically within the range of 100 to 300, in some cases up to 500 µg/kg/min.

For the short-term treatment, e.g. the initial infusion the infusion time typically is less than 60 min, in some cases longer, such as less than 120 min or less than 180 min.

The maintenance dose of said i.v. solution is typically administered during a longer period of time, such as an infusion time of at least 60 min, or at least 2 h, 3 h, 4 h, 5 h or 6 h, in some cases at least 12 or at least 24 hours.

In specific cases the high dose short-term treatment is preferred in cases of blood pressure lowering during aortic dissection or for controlled hypotension to avoid blood loss in ear/nose/throat surgery.

The i.v. solution according to the invention may be advantageously administered intraveneously to patients who could be given only small volumina. Specifically treatment of patients suffering also from cardiac decompensation and/or hyperhydratation and/or renal decompensation and/or hypernatremia and/or hyperchloramic acidosis and/or hyperhydratation is possible.

Said i.v. solution specifically is local tissue tolerant at the infusion site. In particular, it is administered to a patient in a way not causing venous irritation or skin necrosis. Therefore, the specific use of the formulation according to the invention is for preventing local venous irritation or skin necrosis at the infusion site.

According to a specific embodiment, a patient is treated according to the invention who is
  a. suffering from any of acute tachycardia selected from supraventricular tachycardia, ventricular tachycardia or hypertension and non-compensatory sinus tachycardia, atrial fibrillation, atrial flutter in perioperative, postoperative, or other circumstances where short-term control of the ventricular rate is desirable, or
  b. in need of blood pressure lowering during aortic dissection or for controlled hypotension to avoid blood loss in ear/nose/throat surgery or for diagnostic purposes.

According to the invention there is further provided a method of producing a ready-to-use i.v. solution of esmolol hydrochloride by reconstituting a lyophilized powder consisting of pure esmolol hydrochloride with a solvent, characterized in that said solvent is an i.v. solvent devoid of alcohol or a buffer excipient, in an amount necessary to obtain a ready-to-use i.v. solution at a concentration of 20-100 mg/mL.

According to a specific aspect of the invention, there is provided a ready-to-use i.v. solution containing a parenteral formulation of 20-100 mg/mL pure esmolol hydrochloride in an infusion device. Said i.v. solution is specifically ready-to-use without further dilution.

According to another specific aspect of the invention, there is provided a ready-to-use i.v. solution comprising or consisting of a parenteral formulation of 20-100 mg/mL pure esmolol hydrochloride, WFI and/or saline solution, specifically a formulation devoid of any alcohol or further excipients, such as buffer excipients.

Specifically, the i.v. solution is consisting of pure esmolol hydrochloride, WFI and optionally saline.

According to the invention there is further provided a kit or set of parts for preparing a parenteral formulation according to the invention, comprising the components
  a) a lyophilized powder consisting of pure esmolol hydrochloride, and
  b) WFI or saline solution.

Component a) specifically comprises 2500 mg of the powder contained in a 50 mL vial.

The kit optionally further comprises an infusion device suitable for i.v. administration.

DETAILED DESCRIPTION OF THE INVENTION

Specific terms as used throughout the specification have the following meaning.

The term "i.v. solution" as used herein shall mean an aqueous solution suitable for direct administration into the venous circulation of a subject, employing an infusion device, e.g. via a syringe or intravenous catheter or tube. The i.v. solution according to the invention may be freshly prepared by reconstituting the lyophilized powder, or else prepared well before its administration to the subject, specifically when it is storage stable as determined by suitable stability studies.

An iso-osmotic i.v. solution is understood as a solution containing the same concentration of particles and thus exerting equal osmotic pressure as blood. For example, a 0.9% solution of NaCl (Normal Saline) is iso-osmotic with blood. Further examples are 5% glucose, Ringer solution or Ringer lactate solution.

An i.v. solvent is herein understood as a water-miscible solvent for intravenous injection. By using a suitable aqueous medium or carrier as an i.v. solvent, the respective i.v. solution of the active ingredient esomolol hydrochloride is suitably prepared according to the present invention. Suitable i.v. solvents are e.g. water for injection (WFI), glucose solution, glucose and Ringer solution, glucose and saline solution, saline solution, Ringer Lactate solution or Ringer Lactate and saline solution. When an iso-osmotic solvent is used for reconstituting the lyophilized powder of esmolol hydrochloride, the resulting i.v. solution is understood to be an iso-osmotic i.v. solution.

The term "infusion device" as used herein shall mean a device used to administer an intravenous solution, such as a container containing the i.v. solution in the sterile form, and optionally equipped with a seal or septum to enable the sterile discharge of the i.v. solution into a catheter. The infusion device may be suitably in the form of a bag, bottle or syringe, optionally prefilled with the lyophilized powder or the ready-to-use formulation, containing about the volume of administration, e.g. a container of 50 mL, 100 mL, 250 mL, or 500 mL. The infusion device may be of standard materials, including plastic or glass. The device or infusion system may further comprise a suitable catheter, such as a butterfly catheter, e.g. a metal needle with flexible plastic wings and a short length of tubing, which facilitates placement and fixation with tape. The infusion device may also be provided for use with a central catheter placed into a large vein in the neck (internal jugular vein), chest (subclavian vein or axillary vein) or groin (femoral vein), e.g. as used in an intensive care unit. Typically the infusion device as used herein is suitable to drip an i.v. solution into a subject in a controlled way to ensure correct dosing, e.g. through a plastic tube inserted directly into a vein.

The term "local tissue tolerant" with reference to an i.v. solution as used herein shall mean the formulation that is tolerant at the site of injection or infusion, thus minimizing side effects, such as local skin irritations or venous or perivenous irritations, including inflammatory reactions at the infusion site. Specifically the local tissue tolerant i.v. solution has an advantageous adverse reaction profile as determined by preclinical and/or clinical studies. The parenteral formulation according to the invention advantageously has less side reactions than the conventional products, such as skin irritation or phlebitis, in particular in the absence of additives like organic substances such as ethanol, or buffer excipients.

The term "parenteral formulation" with reference to the formulation of esmolol hydrochloride as used herein shall mean a lyophilized powder that is reconstituted to obtain the i.v. solution according to the invention. The formulation specifically is sterile, non-pyrogenic and free from particulate material in the i.v. solution. Specifically the parenteral formulation is sterilized by filtration before lyophilizing. The parenteral formulation may be provided as the lyophilized product or else as a combination product comprising the lyophilized product and the solvent for reconstitution and/or any further means suitably used for reconstituting the product.

The term "pure esmolol hydrochloride" as used herein shall mean esmolol hydrochloride of at least 95% purity, preferably at least 98%, but in average more than 99% purity. The percentage of purity is herein understood as w/w of the dry substance.

The lyophilized powder of pure esmolol hydrochloride is specifically prepared by dissolving the active substance in WFI, sterilized by 0.22 μm filtration and filled into vials. Following lyophilization the vials are closed and sealed. In the absence of additives like organic substances or buffer excipients, the lyophilized powder specifically consists of at least 95%, preferably at least 98%, but in average more than 99% of pure esmolol hydrochloride in the lyophilized form, usually with a residual water content of up to 2%, preferably up to 1%.

The term "ready-to-use" with reference to an i.v. solution according to the invention as used herein shall mean the preparation in the reconstituted form, with standardized concentration and quality, prefilled in the single-use container, such as glass vials, infusion bags or syringes, ready for administration to the patient.

The term "tachycardia" as used herein is understood in the broadest sense, including all disease conditions associated with fast or irregular heart rate, in particular a condition in which the heart contracts at a rate greater than 100/min in adults. Herein tachycardia specifically refers to pathologic tachycardia accompanying anoxia, such as that caused by anemia; congestive heart failure; hemorrhage; or shock. Tachycardia acts to increase the amount of oxygen delivered to the cells of the body by increasing the rate at which blood circulates through the vessels.

The term "direct administration" with reference to an i.v. solution as used herein shall mean the immediate administration, i.e. without further dilution, premixing with other substances or otherwise changing the composition or formulation of the i.v. solution. Such i.v. solution is typically directly discharged from an infusion device and administered via a vascular access port or through a central line.

Therefore, the invention provides for an improved parenteral formulation for use in the treatment of patients. Herein the terms "subject" and "patient" are used interchangeably and refers to human beings in need of such treatment. And further herein the terms "esmolol" and "esmolol hydrochloride" are used interchangeably.

According to the invention the ready-to-use i.v. solution is specifically administered as continuous infusion, but may as well be administered by one or more bolus injections, e.g. single i.v. injections(s). Based on the pharmacological properties esmolol has a fast and short action by which the dose can be quickly adjusted. After the starting dose, e.g. by an initial infusion of the formulation according to the invention, typically a steady state plasma concentration is reached within 5 minutes. However, the therapeutic effect is sooner obtained than the stable plasma concentration. The infusion rate can then be adjusted to obtain the desired pharmacological effect.

The formulation according to the invention may then be employed for a maintenance dose during a suitable administration time. A typical treatment regimen may start with a dose of 500 μg/kg/min for 1 min, followed by a dose of 25-500 μg/kg/min for maintenance infusion or may be initiated by using the maintenance infusion only.

It surprisingly turned out that the typical side effects of local venous skin irritations or inflammatory reactions at the site of injection could be avoided by using the formulation according to the invention. As an example, the i.v. solution based on reconstituting the lyophilized powder in NaCl did not bring about any blushing, erythema, pain, inflammation, induration, phlebitis and thrombosis.

Since the formulation according to the invention provides for the high safety when administering the i.v. solution, there is more flexibility with respect to the treatment dose and regimen. The physician may thus increase the dose as needed, without following a strict scheme that is commonly used to determine the individual tolerability of the i.v. solution in situ during the treatment of the patient.

Despite of using pure esmolol hydrochloride according to the invention, and specifically in the absence of organic solvents, like alcohol, buffering excipients or further auxiliary agents, the formulation according to the invention and the i.v. solution specifically turned out to be surprisingly stable. The formulation in the lyophilized powder form specifically is storage stable at room temperature for at least 12, preferably at least 24, more preferred at least 36 months; the in-use stability for the reconstituted product, i.e. the i.v. solution has proven for at least 6 hours, preferably at least 12 hours, more preferred at least 24 hours.

Stability typically is determined as the percentage of pure esmolol hydrochloride, which is at least 95%, and the absence of contaminating degradation products of esmolol hydrochloride.

Specific examples relate to the preparation of the lyophilized powder of pure esmolol hydrochloride, the reconstitution to prepare the i.v. solution and the protocol to its clinical use.

The foregoing description will be more fully understood with reference to the following examples. Such examples are, however, merely representative of methods of practicing one or more embodiments of the present invention and should not be read as limiting the scope of invention.

EXAMPLES

Examples below illustrate the materials and methods used to prepare and administer the formulations and i.v. solutions according to the invention.

Example 1: Preparation of the Lyophilized Powder of Pure Esmolol Hydrochloride Pure esmolol hydrochloride is added to Water for Injections and the solution is stirred until it is homogenous. The pH is checked and if necessary adjusted to 4.0 to 6.0. The final product solution is sterile filtered, filled into vials and finally lyophilized by a defined freeze-drying program.

Example 2: Reconstitution of the Lyophilized Powder of Example 1 to Prepare the i.v. Solution The lyophilized powder is reconstituted in 50 mL of reconstitution agent to receive a final product concentration of 50 mg/mL. In-use stability data are available with the below mentioned reconstitution agents showing stability of the reconstituted solution up to 24 hours at room temperature:

0.9% NaCl solution
Glucose 5% solution
Ringer's lactate solution
Glucose 5% in Ringer's solution
Glucose 5% in 0.9% NaCl solution
Glucose 5% in Ringer's lactate solution In addition, in-use stability data are available with the solvents 0.9% NaCl solution, 5% Glucose solution and Ringer's lactate solution for a final product concentration of 10 mg/mL (2500 mg/250 mL). All three solvents lead to a stable product solution up to 24 h at room temperature.

The lyophilized powder is reconstituted within 15 sec with 50 mL of Water for Injections.

Studies regarding reconstitution time with less than 50 mL reconstitution volume were performed with 5% glucose and 0.9% NaCl solution.

The reconstitution time in 5 mL of 5% glucose solution was defined with 90 sec, in 10 mL the reconstitution time could be reduced to 60 sec.

The reconstitution time in 5 mL of 0.9% NaCl solution was defined with 75 sec, in 10 mL the reconstitution time was reduced to 50 sec.

Example 3: Administration of a Reconstituted Solution of Example 2

The reconstituted solution was applied intravenously using large superficial arm veins at doses between 25 to 300 µg/kg/min up to 24 h without the induction of local reactions such as pain, reddening, erythema, blushing, thrombophlebitis or induration and thrombosis.

The invention claimed is:

1. A method of treating a patient suffering from tachycardia, comprising the steps of:
    reconstituting a lyophilized powder consisting of pure esmolol hydrochloride with water for injection (WFI) or an aqueous saline solution to obtain a ready-to-use intravenous (i.v.) solution of esmolol hydrochloride at a concentration of 50 mg/mL, wherein the solution is free of alcohol and buffer excipients; and
    administering the i.v. solution to the patient,
    thereby treating the tachycardia.

2. The method of claim 1, wherein the i.v. solution has a pH of 4.5 to 5.0.

3. The method of claim 1, wherein the i.v. solution is administered as a continuous infusion.

4. The method of claim 1, wherein the i.v. solution is administered as a maintenance infusion at a dose of at least 25 µg/kg/min.

5. The method of claim 4, wherein the i.v. solution is administered following an initial infusion of the i.v. solution at a dose of at least 300 µg/kg/min.

6. The method of claim 1, wherein the i.v. solution is local tissue tolerant at the infusion site, thereby preventing local venous irritation or skin necrosis at the infusion site.

7. The method of claim 1, wherein the patient is:
    a. suffering from a condition selected from the group consisting of supraventricular tachycardia, ventricular tachycardia, non-compensatory sinus tachycardia, atrial fibrillation, and atrial flutter, or
    b. in need of blood pressure lowering during aortic dissection or for controlled hypotension to avoid blood loss in ear/nose/throat surgery or for diagnostic purposes.

8. The method of claim 1, wherein the patient is experiencing one or more conditions selected from the group consisting of cardiac decompensation, renal decompensation, hypernatremia, hyperchloramic acidosis, and hyperhydratation.

9. The method of claim 1, wherein the lyophilized powder consisting of pure esmolol hydrochloride is reconstituted with an aqueous saline solution.

10. The method of claim 1, wherein the lyophilized powder consisting of pure esmolol hydrochloride is reconstituted with water for injection (WFI).

* * * * *